(12) United States Patent
Elsik et al.

(10) Patent No.: US 9,426,987 B2
(45) Date of Patent: Aug. 30, 2016

(54) PESTICIDE FORMULATION WITH STREAMING BIREFRINGENCE

(75) Inventors: Curtis M. Elsik, The Woodlands, TX (US); Joe C. Arzola, Austin, TX (US); Howard M. Stridde, George West, TX (US); Alan J. Stern, Magnolia, TX (US)

(73) Assignee: HUNTSMAN PETROCHEMICAL LLC, The Woodlands, TX (US)

( * ) Notice: Subject to any disclaimer, the term of this patent is extended or adjusted under 35 U.S.C. 154(b) by 1086 days.

(21) Appl. No.: 13/364,774

(22) Filed: Feb. 2, 2012

(65) Prior Publication Data

US 2012/0135865 A1    May 31, 2012

Related U.S. Application Data

(63) Continuation of application No. 12/441,834, filed as application No. PCT/US2007/079018 on Sep. 20, 2007, now abandoned.

(60) Provisional application No. 60/826,717, filed on Sep. 22, 2006.

(51) Int. Cl.
*A01N 43/00* (2006.01)
*A61K 31/33* (2006.01)
*A01N 25/30* (2006.01)

(52) U.S. Cl.
CPC ..................................... *A01N 25/30* (2013.01)

(58) Field of Classification Search
None
See application file for complete search history.

(56) References Cited

U.S. PATENT DOCUMENTS

| 5,037,653 A | 8/1991 | Dawson |
| 5,317,042 A | 5/1994 | Narayanan |
| 5,468,718 A | 11/1995 | Burval et al. |
| 5,538,936 A | 7/1996 | Hermansky |
| 6,365,551 B1 | 4/2002 | Wright et al. |
| 6,407,042 B1 | 6/2002 | Ward et al. |
| 6,528,070 B1 | 3/2003 | Bratescu et al. |
| 6,544,930 B2 | 4/2003 | Wright |
| 6,881,707 B2 | 4/2005 | Howat et al. |
| 2002/0160918 A1* | 10/2002 | Lewis et al. ................... 504/363 |
| 2003/0050194 A1* | 3/2003 | Hopkinson et al. ........... 504/363 |
| 2006/0040826 A1 | 2/2006 | Eaton et al. |

FOREIGN PATENT DOCUMENTS

| WO | WO-0111958 A1 | 2/2001 |
| WO | WO-2006023431 A2 | 3/2006 |

OTHER PUBLICATIONS

Roundup Pro Herbicide (Product Label, 2003).*
Diamond et al (Effects of Surfactants on the Toxicity of Glyphosate, with Specific Reference to RODEO, 1997).*
Platz et al (Langmuir 11:4250-4255, 1995).*

* cited by examiner

*Primary Examiner* — Craig Ricci
(74) *Attorney, Agent, or Firm* — Huntsman International LLC

(57) ABSTRACT

A pesticide composition exhibiting streaming birefringence and methods for making the pesticide composition are disclosed. In one embodiment, the pesticide composition comprises an active ingredient and a surfactant adjuvant.

10 Claims, 2 Drawing Sheets

PESTICIDE FORMULATION WITH STREAMING BIREFRINGENCE

CROSS-REFERENCE TO RELATED APPLICATIONS

Figure 1:
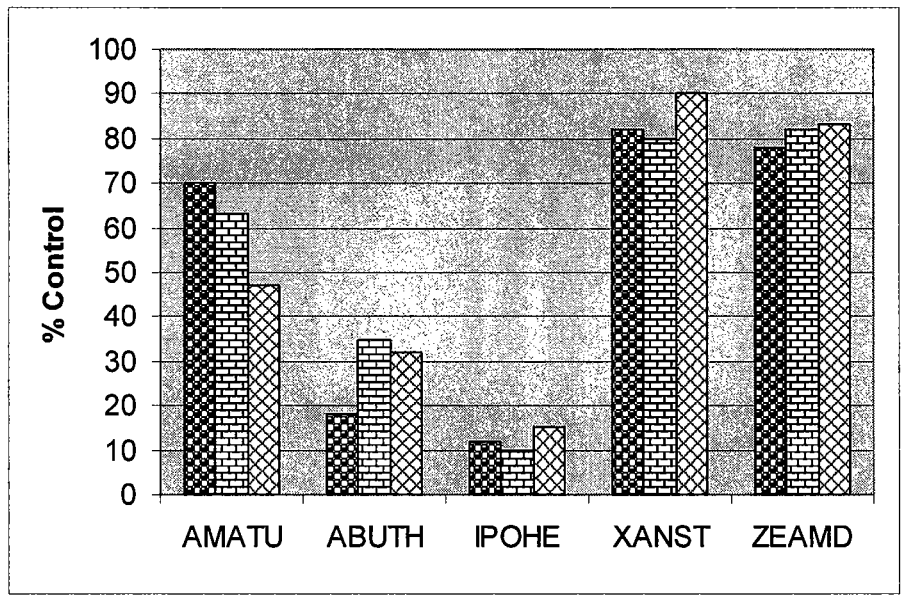

This application is a continuation of U.S. application Ser. No. 12/441,834, filed Mar. 18, 2009, which is a U.S. national stage application of PCT Application PCT/US07/79018, filed Sep. 20, 2007, which claims the benefit of U.S. Provisional Application Ser. No. 60/826,717, filed on Sep. 22, 2006.

FIELD OF THE INVENTION

This invention relates to the field of pesticide formulations and more specifically to pesticide formulations that exhibit streaming birefringence.

BACKGROUND OF THE INVENTION

Pesticide compositions have been used in agrochemical and related applications. Pesticide compositions typically include an active ingredient as well as an adjuvant. Active ingredients include herbicides such as glyphosate. An example of a typical adjuvant is a surfactant. Pesticide compositions are disclosed in U.S. Pat. Nos. 6,365,551; 6,881,707; 6,544,930; 5,468,718; and WO 2006/023431, which are each incorporated by reference herein in its entirety.

Drawbacks to such pesticide compositions include retention of the spray drops on the target surface and incomplete incorporation into the target pest. Further drawbacks include the limited time the active ingredient has to move into the pest due to the spray solution solidifying.

Consequently, there is a need for an improved pesticide composition. Further needs include an improved pesticide composition having streaming birefringence. Additional needs include a pesticide composition having an improved retention and time for active diffusion.

SUMMARY OF THE INVENTION

These and other needs in the art are addressed by a pesticide composition comprising an active ingredient and a surfactant adjuvant, and which exhibits streaming birefringence.

In an embodiment, a pesticide composition includes a super high load mixed salt glyphosate soluble liquid formulation. An embodiment of a pesticide composition may include one or more active ingredients and one or more surfactants with the final formulation exhibiting streaming birefringence.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

FIG. 1 is a graph indicating the percent control of weed growth at ten days after treatment with an embodiment of the present invention and Round Up® Original herbicide;

FIG. 2 is a graph indicating the percent control of weed growth at 27 days after treatment with the same embodiments as in FIG. 1 and Round Up® Original herbicide; and FIGS. 3A-3D are photographs of a sample bottle containing an embodiment of a pesticide composition that exhibits streaming birefringence.

DETAILED DESCRIPTION OF THE INVENTION

In an embodiment, a pesticide composition exhibiting streaming birefringence includes an active ingredient and a surfactant adjuvant blend. Thus active ingredients may be formulated in a new thermodynamic equilibrium phase. It is to be understood that streaming birefringence (e.g., flow birefringence) refers to birefringence that is induced by flow in liquids, solutions and dispersions of optically anisotropic, anisometric or deformable flow molecules or particles due to a non-random orientation of the molecules or particles. Without being limited by theory, a pesticide composition that exhibits streaming birefringence has molecules or particles that are randomly oriented at rest hence the composition is isotropic and does not exhibit birefringence. But during flow the molecules or particles are not randomly oriented hence the composition is anisotropic and exhibits birefringence.

For instance, a pesticide composition that exhibits streaming birefringence may include an active ingredient that is combined with elongated surfactant micelles; the elongated surfactant micelles may or may not contain a solubilized oil phase. At rest, the pesticide composition is isotropic and does not exhibit birefringence because, in theory, the micelles are randomly oriented. But when the pesticide composition is disturbed or moved in any manner, the movement may align the elongated micelles along the flow field creating an optically anisotropic system that exhibits birefringence. This dynamic structuring may be observed by placing a composition between cross polarized films that are lighted from behind by a light module. At rest, a pesticide composition having streaming birefringence is isotropic and dark. Under movement however the composition is anisotropic, and the material may be visually observed (e.g. bright or lighted) between the cross polarized films. In other words, the streaming birefringent phase is illuminated in contrast to the dark static isotropic phase.

Active ingredients may include any chemical substance that has pesticidal properties. Without limitation, examples of active ingredients having pesticidal properties include herbicides, insecticides, fungicides, biocides, molluscicides, algaecides, plant growth regulators, anthelmintics, rodenticides, nematocides, acaricides, amoebicides, protozoacides, or combinations thereof. Without limitation, further examples of such pesticides include triazine herbicides such as simazine, atrazine, terbuthylazine, terbutryn, prometryn and ametryn; urea herbicides such as diuron and fluometuron; sulfonyl urea herbicides such as chlorsulfuron, metsulfuron methyl, nicosulfuron and triasulfuron; sulfonanilide herbicides such as flumetsulam; organophosphate insecticides such as azinphos methyl, chlorpyrifos, sulprofos and azamethiphos; carbamate insecticides such as aldicarb, bendiocarb, carbaryl and fenobucarb; acid amide herbicides such as metolachlor and alachlor; fungicides such as dimethomorph, benomyl, carbendazim, mancozeb, and tebuconazole; and acaricides such as propargite. Lists of pesticides are disclosed in the Crop Protection Dictionary (contained in the Meisterpro Crop Protection Handbook) and the British Crop Protection Council: The Pesticide Manual, which are each incorporated herein by reference in their entirety. It is to be understood that the pesticide composition may include any combination of active ingredients suitable for a desired application. In an embodiment, the active ingredients include an herbicide such as glyphosate. In some embodiments, the active ingredients comprise glyphosate, one or more salts thereof, or combinations thereof. For example, in agricultural applications, acceptable glyphosate salts include potassium salts, isopropylamine salts, ammonium salts, sodium salts and monoethanol amine (MEA) salts, although embodiments are not limited thereto. In some embodiments, the active ingredients include an insecticide. In addition, embodiments include the active ingredients including a fungicide.

The pesticide composition may contain any amount of the active ingredient suitable for a desired application. In an embodiment, the pesticide composition contains from about 1.0 wt. % to about 65.0 wt. % of the active ingredient, alternatively from about 5.0 wt. % to about 55.0 wt. % of the active ingredient.

The pesticide composition may contain any surfactant adjuvant suitable for providing streaming birefringence. In an embodiment, the surfactant adjuvant includes an alkylamine alkoxylate phosphate ester such as an alkylamine ethoxylate phosphate ester or an alkylamine propoxylate phosphate ester. One example is a phosphate ester of a tallow amine ethoxylate, although embodiments are not limited thereto. Other alkylamine alkoxylate esters include, without limitation, soya- and coco-amine alkoxylate phosphate esters. In another embodiment the surfactant adjuvant includes a lard dimethylaminopropylamine amidoamine oxide surfactant. Additional embodiments may include other surfactant adjuvants such as an alkylpolysaccharide, a mono- or di-alkyl sulphosuccinate derivative, a nonionic alcohol alkoxylate surfactant, and an anionic surfactant such as an alkylbenzene sulfonate. It is to be understood that the surfactant adjuvants may include any one or combination of surfactants. In an embodiment, the surfactant adjuvant comprises a blend of a phosphate ester of a tallow amine ethoxylate combined with an alkylpolysaccharide, alternatively phosphate esters of a tallow amine ethoxylate. The pesticide composition may contain any amount of the surfactant adjuvants suitable for facilitating dilution and providing streaming birefringence. In an embodiment, the pesticide composition contains from about 0.5 wt. % to about 10.0 wt. % of the surfactant adjuvants.

In an embodiment, the active ingredients are dispersed in an aqueous medium by any suitable means. For instance, the active ingredients may be dispersed by stirring, mixing, blending, and the like. In an additional embodiment, the active ingredients are dispersed in or as an oil phase. In an embodiment, the active ingredients are a solid dispersed in a homogeneous continuous phase.

In an alternative embodiment, the pesticide composition contains additional adjuvants. It is to be understood that an adjuvant refers to a subsidiary additive in a mixture that contributes to the effectiveness of the primary ingredient. In an embodiment, the adjuvants include an oil-based adjuvant. Any oil-based adjuvant suitable for use in agrochemical applications may be used. Without limitation, examples of suitable oil-based adjuvants include crop oils, crop oil concentrates, vegetable oils, modified vegetable oils, or combinations thereof. The pesticide composition may contain any amount of the oil-based adjuvant suitable for a desired use. In some embodiments, the oil-based adjuvant facilitates efficacy of the active ingredient. In an embodiment, the pesticide composition contains from about 1.0 wt. % to about 15.0 wt. % of adjuvant. Other examples of adjuvants (e.g., non oil-based) include silicon-based adjuvants, sticker adjuvants, extender adjuvants, plant penetrant surfactants, compatibility agent adjuvants, mineral control adjuvants, drift retardant adjuvants, defoaming agent adjuvants, thickener adjuvants, solvent adjuvants, and fertilizer-based adjuvants. In an embodiment, the pesticide composition does not contain an inert adjuvant.

In other alternative embodiments, the pesticide composition may also contain formulation aids. Without limitation, examples of suitable formulation aids include antifreeze, dyes, thickening agents, preservatives, anti-foaming agents, ultraviolet stabilizers, and pH adjusting agents. The pesticide composition may contain any amount of the formulation aids suitable for a desired application. In an embodiment, the pesticide composition may contain from about 0.1 wt. % to about 10.0 wt. % of the formulation aids.

In an embodiment, the pesticide composition is applied in any desirable application such as in agricultural applications. For instance, the pesticide composition may be applied to control weeds, insects, and/or fungi. In addition, the pesticide composition may be applied to insects, crops, soils, and the like. The pesticide composition may be applied by any suitable method. In some embodiments, the pesticide composition is applied directly to the target (e.g., the insect, soil, and/or crop) or is diluted before such application.

In some embodiments, the pesticide composition is a super highly loaded glyphosate composition that comprises greater than about 50 wt. % glyphosate salt comprising a mixture of glyphosate salts and also comprising one or more surfactants. In embodiments, the pesticide composition is a super highly loaded glyphosate composition comprising greater than about 50 wt. % glyphosate salt comprising a mixture of potassium and isopropylamine (IPA) glyphosate salts, the phosphate ester of a tallow amine ethoxylate, and an alkylpolysaccharide. The potassium and IPA may be in any ratio suitable for an agrochemical use. In an embodiment, the pesticide composition comprises a weight ratio of potassium to IPA salt from about 91:9 to about 99:1.

The pesticide composition exhibiting streaming birefringence has many advantages over conventional compositions. For instance, the composition system can be in a single-phase thermodynamic equilibrium, which may provide long term physical stability in comparison to non thermodynamic or multiple-phase equilibrium systems. Further advantages include the elongated micelles of the pesticide composition showing that the system is very close to a hexagonal liquid crystal phase transition. The presence of a liquid crystal phase provides many advantages to a pesticide formulation. Such advantages include increased efficacy due to enhanced translocation of the active ingredient, drift control due to increased elongational viscosity of the spray solution, increased active ingredient (a.i.) diffusion that will result from keeping the spray from solidifying for extended times, and improved sticking of the spray solution to the target that may result from the surface chemistry of the surfactant phase behavior. Without being limited by theory, since the system being sprayed originally existed as elongated micelles, the sprayed solution may form a liquid crystal during drying faster than a system that originally consisted of spherical micelles. Additional advantages of the pesticide composition include that the elongated micelles may increase retention of the spray drop on the target surface due to increased viscosity.

It is to be understood that other pesticidal active ingredients may be formulated into a streaming birefringent phase. In addition, the elongated micelles may be formulated into formulation types other than soluble liquids.

To further illustrate various illustrative embodiments of the present invention, the following examples are provided.

EXAMPLES

Example 1

Formulations Including an Alkylamine Alkoxylate Phosphate Ester Surfactant Adjuvant During a project to investigate the maximum loading possible for a soluble liquid glyphosate formulation, a composition was discovered that exhibited streaming birefringence. A mixed K:IPA salt of glyphosate with a high ratio of K was used with a surfactant blend of two surfactants. The first surfactant in the blend was a phosphate ester of a tallow amine ethoxylate. The surfactant chemistry for phosphate esters of tallow amine is disclosed in WO 01/11958A1, which is incorporated by reference herein in its entirety. The second surfactant in the blend was an alkylpolysaccharide.

Referring to Table 1, below, several pesticide formulations are listed in which the active ingredient was potassium glyphosate 58.0 wt. % active ingredient (ai), or potassium glyphosate manufacturer use concentrate, which corresponds to 47.5 wt. % glyphosate acid equivalent (ae), together with isopropylamine glyphosate 62.0 wt. % ai. A surfactant used in Formulations 1-7 and 9 was the Surfactant PET5, which is a phosphate ester of a 5-mole-ethoxylate of tallow amine; another surfactant used in each formulation was TERWET® 3001 surfactant, which is an alkylpolysaccharide. Both surfactants were obtained from Huntsman (The Woodlands, Tex.) as experimental Surfactant PET5 and TERWET® 3001 respectively.

TABLE 1

| | Formulation No. | | | | | | | | |
|---|---|---|---|---|---|---|---|---|---|
| Ingredient (grams) | 1 | 2 | 3 | 4 | 5 | 6 | 7 | 8 | 9 |
| K Glyphosate (58% ai) | 87.5 | 87.5 | 87.5 | 87.5 | 87.5 | 87.5 | 87.5 | 87.5 | 89 |
| IPA Glyphosate (62% ai) | 3.3 | 3.3 | 3.3 | 3.3 | 3.3 | 3.3 | 3.3 | 3.3 | 3.4 |
| TERWET ® 3001 | 2.6 | 3.6 | 4.6 | 5.6 | 6.6 | 7.6 | 8.6 | 9.2 | 4.6 |
| Surfactant PET5 | 6.6 | 5.6 | 4.6 | 3.6 | 2.6 | 1.6 | 0.6 | 0 | 3 |
| Total w/w % | 100 | 100 | 100 | 100 | 100 | 100 | 100 | 100 | 100 |

Potassium and isopropylamine (IPA) glyphosate salts are available from sources such as Monsanto (St. Louis, Mo.), Nufarm (Victoria, Australia), Albaugh (Ankeny, Iowa), or Cheminova (Lemvig, Denmark). Alternatively, potassium glyphosate may be prepared by neutralizing n-phosphonomethylglycine acid with potassium hydroxide, and IPA glyphosate may be prepared by neutralizing n-phosphonomethyl glycine acid with isopropyl amine.

Generally, the formulations of Table 1 were made by mixing the glyphosate salts and surfactant(s) in a sample bottle until uniform. In some instances a sample was heated to facilitate mixing and cooled to room temperature (RT).

Glyphosate formulations that are considered for commercial introduction typically are physically stable, homogeneous at specified temperatures, have a cloud point greater than 50° C., and have a viscosity sufficiently low to be pumped. Thus, glyphosate Formulations 1-9 were analyzed for homogeneity and cloud point. Homogeneity was established by visually inspecting the formulations at room temperature (RT) for clarity. Cloud point was determined by mixing each formulation while heating until it became cloudy. The formulation was then removed from the heat source and the temperature was measured in degrees Celsius (° C.) when the formulation regained clarity. Formulations 1-9 were also examined to see if they exhibited streaming birefringence. The streaming birefringence of a formulation was established by visually inspecting a sample bottle containing the formulation that was placed between two cross polarized plates, which were lighted from behind. The formulations were visually inspected both at rest and while agitated. The results for each formulation are indicated in Table 2.

TABLE 2

| | Formulation No. | | | | | | | | |
|---|---|---|---|---|---|---|---|---|---|
| | 1 | 2 | 3 | 4 | 5 | 6 | 7 | 8 | 9 |
| RT Solution Clear? | No | Yes | Yes | Yes | Yes | Yes | Yes | Yes | Yes |
| Cloud Point (° C.) | — | 49 | 59 | 69 | 94 | >97 | >97 | >97 | 74 |
| Streaming Birefringence? | n/a | Yes | Yes | Yes | Yes | Yes | No | No | Yes |

Referring to Table 2, it is shown that the combination of a phosphate ester of a tallow amine ethoxylate and an alkylpolysaccharide provide both potassium glyphosate compatibility and improved bioefficacy. In comparison, an alkylpolysaccharide alone (e.g. Formulation 8) or in combination with a low concentration of a phosphate ester of a tallow amine ethoxylate (e.g. Formulation 7) did not show such improvement. Moreover, Formulation 1 was the only formulation of Table 1 that was not clear at room temperature. In fact, it separated into two phases and it was turbid. Because Formulation 1 was not acceptable for commercialization its cloud point was not established and it was not tested for birefringence. Of the formulations in which cloud point was established, only Formulation 2 had a borderline cloud point. The cloud points for Formulations 3 and 4 were acceptable for a commercial product and the cloud points for Formulations 5-9 were much greater than 50° C. The cloud points for Formulations 6-8 were greater than 97° C. as they were clear when heated to this temperature. To avoid boiling, these formulations were not heated above 97° C. Formulations 2-6 and 9 exhibited streaming birefringence; Formulations 7 and 8 did not. Furthermore, of the formulations that exhibited streaming birefringence, Formulations 2-4 were brighter to the eye than the others.

Generally, Formulations 3 and 4 provided good stability, which is indicated, for example, by cloud point. Additionally, Formulation 3 passed three freeze/thaw cycles to −10° C. and a four week freeze at −10° C. without any precipitation, which also indicates good stability. Notably, this formulation stayed fluid at −10° C. Moreover, each formulation of Table 1 had acceptable viscosity. For example, the viscosity of Formulation 4 was 170 centipoise (cP) at 20° C. But the density of Formulation 4 was measured at 1.403 g/ml, which corresponds to a relatively heavy 1,403 g/L.

As can be gathered from the results above, formulations were loaded with glyphosate at a high level, physically stable, homogeneous at room temperature, and had an acceptable cloud point and viscosity. For example, potassium glyphosate made up about 51 wt. % of the final formulation of Formulations 1-9 with K:IPA mixed salt present at a 96:4 ratio of mixed salt. Notably, Formulation 4 contained 583 grams acid equivalent (gae)/L glyphosate from the K salt and 22 gae/L glyphosate from the IPA salt. A total of 605 gae/L glyphosate in Formulation 4 is significantly above the highest loaded commercially available formulation of 540 gae/L, of which there are several. Formulation 9 was similar to Formulation 4, but the glyphosate loading was pushed to an even higher level of 615 gae/L. The surfactant loading in these formulations was approximately 130 g/L. The surfactant was preferred to be fully loaded since there was such a high loading of glyphosate. As is shown herein, liquid glyphosate formulations can be loaded at or above 600 gae/L glyphosate, be physically stable (even at temperatures as low as −10° C.), and have a relatively low viscosity (e.g. 423 cP at 5° C.).

Example 2

Field Trials with Formulations No. 3 and 9

Field trials were run on Formulations No. 3 and 9 of Table 1, above, and Roundup® Original (RU Orig.) herbicide (which was applied at half label rates) to test for phytotoxicity and glyphosate efficacy. Roundup® Original is obtainable from Monsanto, St. Louis, Mo. Generally, plants were grown on test plots that were thirty feet long by ten feet wide and that included four thirty-inch width rows of plants. Three replicate test plots were used for each herbicide tested. The crop chosen for testing was a Roundup Ready® soybean (Monsanto, St. Louis, Mo.), which were at the trifoliate stage, approximately 12 inches tall. The weeds in the test plots were 6-12 inches tall. The weeds studied included Tall Waterhemp (AMATU), Velvetleaf (ABUTH), Ivyleaf Morningglory (IPOHE), Common Cocklebur (XANST), and Dent Corn (ZEAMD). One set of test plots was left unsprayed to act as a control—to monitor prevailing weed growth. Formulations were applied using flat fan nozzles at 30 pounds per square inch gauge (psig) spray pressure and 10 gallons/acre spray volume. The plots were visually observed at 10, 19, and 27 days after treatment (DAT) to determine weed control. No soybean phytotoxicity was observed for any of the samples.

TABLE 3

| Days After Treatment (DAT) | Formulation | Weed Control % | | | | |
|---|---|---|---|---|---|---|
| | | AMATU | ABUTH | IPOHE | XANST | ZEAMD |
| 10 | No. 3 | 70 | 18 | 12 | 82 | 78 |
| | No. 9 | 63 | 35 | 10 | 80 | 82 |
| | RU Orig. | 47 | 32 | 15 | 90 | 83 |
| 19 | No. 3 | 73 | 27 | 17 | 97 | 93 |
| | No. 9 | 70 | 38 | 12 | 90 | 85 |
| | RU Orig. | 45 | 33 | 13 | 100 | 95 |
| 27 | No. 3 | 70 | 18 | 17 | 100 | 100 |
| | No. 9 | 63 | 30 | 8 | 98 | 100 |
| | RU Orig. | 47 | 30 | 13 | 100 | 100 |

Figure 2:
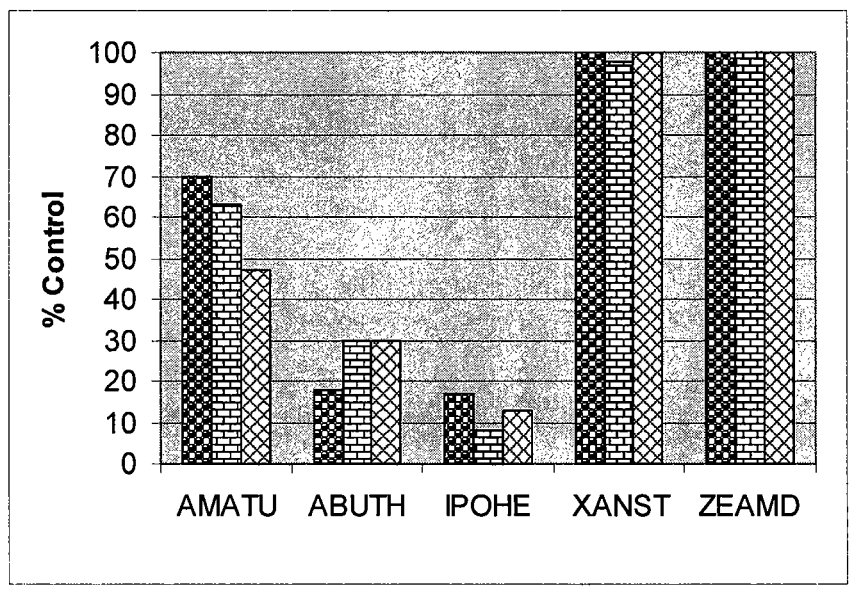
Figure 3A:
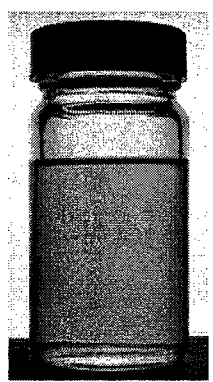
Figure 3B:
Figure 3C:
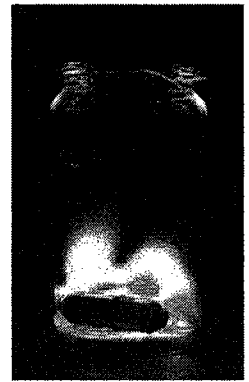
Figure 3D:

Referring to Table 3 and FIGS. 1 and 2, weed control is reported as a percent (%) of control. In the Figures, the weed types are indicated on the x-axis and the percent control is on the y-axis. The results for the % control of each weed type are shown in FIGS. 1 and 2 by depicting Formulation No. 3 as the left-most bar, Formulation No. 9 as the middle bar, and RU Orig. as the right-most bar. Generally, the results were obtained by observing the growth of weeds on each plot and averaging the observations for the three test plots that were sprayed with a particular herbicide. This average was compared to the average growth of that weed type in the control plots. For example, if the growth of AMATU on the control plots is taken as 100%, Formulation No. 3 reduced the growth of that weed type by 70% at 10 and at 27 DAT. In other words, only 30% of AMATU was observed growing on the test plots sprayed with Formulation No. 3 as compared to the test plots left unsprayed.

As is shown in Table 3 and FIG. 1, Formulations 3 and 9 both performed better at 10 DAT than RU Orig. in controlling AMATU (Tall Waterhemp) growth. Furthermore, all three formulations were effective at controlling XANST (Common Cocklebur) and ZEAMD (Dent Corn) growth at 10 DAT. Similar results were observed at 19 DAT, which is shown in Table 3. Referring to FIG. 2 and Table 3, it is shown that Formulations 3 and 9 both maintained a better performance at 27 DAT than RU Orig with respect to AMATU and that all three formulations were very effective at controlling the growth of XANST and ZEAMD.

Example 3

Additional Pesticide Formulations

Pesticide compositions that exhibit streaming birefringence are not limited to a particular surfactant chemistry or active ingredient. For example, the surfactant compositions and/or the active ingredient compositions of Formulations 10-12 of Table 4, below, differ from that of Formulations 1-9.

Referring to Table 4, the active ingredient of Formulation 10 is potassium glyphosate 58.0 wt. % ai, which corresponds to 47.5 wt. % glyphosate ae. Generally, Formulation 10 was made by adding 15 grams of a lard DMAPA N-oxide surfactant to 85 grams of a 58% solution of potassium glyphosate in water. The blend was gently warmed to about 50° C. and it was stirred until uniform. The active ingredients of Formulations 11 and 12 were Metolachlor (98.7% ai, liquid technical) and Tebuconazole (96.5% ai, solid powder technical) respectively. Generally, Formulations 11 and 12 were made by mixing 0.05 grams of the respective active ingredient with 19.95 grams of Formulation 3 to make a 0.25% w/w % pesticide formulation.

TABLE 4

| | Formulation No. | | |
|---|---|---|---|
| Ingredient (grams) | 10 | 11 | 12 |
| K Glyphosate (58% ai) | 85 | 17.45 | 17.45 |
| IPA Glyphosate (62% ai) | — | 0.66 | 0.66 |
| Metolachlor (98.7% ai) | — | 0.05 | — |
| Tebuconazole (96.5% ai) | — | — | 0.05 |
| TERWET ® 3001 | — | 0.92 | 0.92 |
| Surfactant PET5 | — | 0.92 | 0.92 |
| Lard DMAPA amidoamine oxide surfactant | 15 | — | — |
| Total (grams) | 100 | 20 | 20 |

Potassium glyphosate may be obtained from Monsanto (St. Louis, Mo.), Nufarm (Victoria, Australia), Albaugh (Ankeny, Iowa), or Cheminova (Lemvig, Denmark), or it may be prepared as explained above. Metolachlor may be obtained from Syngenta (Greensboro, N.C.) or DuPont (Newark, Del.), whereas Tebuconazole may be obtained from Bayer (Kansas City, Mo.) or Makhteshim-Agan (New York, N.Y.). TERWET® 3001 surfactant and experimental Surfactant PET5 were obtained from Huntsman (The Woodlands, Tex.).

The lard DMAPA amidoamine oxide surfactant was synthesized by combining partially hydrogenated lard (125 grams) with dimethylaminopropylamine (DMAPA) (49 grams) in a reactor vessel, and heating the mixture to 160° C. The heated mixture was stirred under a nitrogen atmosphere for 6 hours. Excess DMAPA was stripped out of the reactor by passing a stream of nitrogen over the reaction mixture while continuing to stir at 160° C. The mixture was cooled to 50° C., and 35% hydrogen peroxide solution (45 grams) was carefully added. After 1 hour of continuous stirring, the lard-amidoamine N-oxide was ready for use. DMAPA is available from Huntsman (The Woodlands, Tex.), hydrogen peroxide is available from Sigma-Aldrich (St. Louis, Mo.), and partially hydrogenated lard was obtained from H.E. Butt Grocery Company (San Antonio, Tex.).

Referring to Table 5, below, Formulation 10 was analyzed for homogeneity and cloud point in the same manner as Example 1. Formulation 10 was crystal clear and had a cloud point of 90° C. In contrast, Formulations 11 and 12 were hazy so their cloud points were not obtained. Nevertheless each formulation of Table 4 exhibited streaming birefringence under cross-polarized light.

TABLE 5

| | Formulation No. | | |
|---|---|---|---|
| | 10 | 11 | 12 |
| RT Solution Clear? | Yes | Hazy | Hazy |
| Cloud Point (° C.) | 90 | n/a | n/a |
| Streaming Birefringence? | Yes | Yes | Yes |

Formulation 11 was an oil-in-water emulsion that formed a second discontinuous phase suspended in a continuous phase. The continuous phase of this formulation exhibited streaming birefringence. Formulation 12 was a solid suspended in a continuous phase. After standing at room temperature for about 20 hours, streaming birefringence was observed in the equilibrium continuous aqueous phase. Thus, Formulations 11 and 12 show that a second discontinuous phase can be suspended in a thermodynamic equilibrium composition that exhibits streaming birefringence without destroying the elongated micelle structure of the continuous phase that produces the streaming birefringence. The second dispersed phase can either be an oil-in-water emulsion such as Formulation 11 or a solid suspension, such as Formulation 12.

Referring to FIG. 3, photographs of Formulation 10 are shown. FIG. 3A is a photograph of Formulation 10 in ambient light and at rest. As can be seen in FIG. 3A, Formulation 10 is a clear liquid that is physically homogeneous. FIG. 3B is a photograph of the same formulation at rest between crossed polarizing films and is lighted from behind the films. Only the curvature of the glass sample bottle can be partially seen in this photograph; the formulation is not birefringent at rest. In contrast, referring to FIGS. 3C and 3D, the formulation shows birefringence under very slight mixing with a magnetic stirrer (FIG. 3C) and more birefringence with slightly faster stirring (FIG. 3D). The only difference between FIGS. 3B and 3C and 3D is the degree of flow. In theory, the elongated micelles of the surfactant are randomly oriented at rest, producing an isotropic index of refraction, and therefore no birefringence. Thus, the sample is dark when placed between cross-polarized plates. When flow is induced, however, the elongated micelles align themselves with the flow field to create a structured liquid system. This structuring can be seen as birefringence, or the bright part of the sample near the stir bar at the bottom of the sample. The oriented elongated micelles have produced a liquid with an anisotropic refractive index. In other words, the index of refraction changes with direction. Comparing FIG. 3C with FIG. 3D, as more of the sample is structuring under increased agitation, more of the sample is birefringent and bright.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A pesticide composition comprising:
   an active ingredient comprising a glyphosate and/or one or more glyphosate salts; and
   a surfactant adjuvant blend, comprising a phosphate ester of a tallow amine ethoxylate and an alkylpolysaccharide, wherein the pesticide composition contains about 0.5 weight percent to about 10 weight percent of the surfactant adjuvant blend, and wherein the pesticide composition exhibits streaming birefringence and does not exhibit birefringence when at rest.

2. The pesticide composition of claim 1, wherein the surfactant adjuvant further comprises a lard dimethylaminopropylamine amidoamine oxide surfactant.

3. The pesticide composition of claim 1, wherein the pesticide composition comprises greater than 50 wt. % glyphosate salt.

4. The pesticide composition of claim 3, wherein the glyphosate salt comprises a mixture of potassium and IPA.

5. The pesticide composition of claim 1, wherein the pesticide composition comprises a glyphosate salt comprising a mixture of potassium and IPA.

6. The pesticide composition of claim 1, wherein the pesticide composition comprises one or more glyphosate salts, and the loading of said one or more glyphosate salts in said pesticide composition is at least 600 grams acid equivalents per liter glyphosate.

7. The pesticide composition of claim 1, wherein the pesticide composition comprises about 50 wt. % glyphosate salt.

8. The pesticide composition of claim 1, wherein the amount of the phosphate ester of a tallow amine ethoxylate is between 1.6 and 5.6 weight percent of the pesticide composition.

9. The pesticide composition of claim 8, wherein the amount of the alkylpolysaccharide is between 3.6 and 7.6 weight percent of the pesticide composition.

10. The pesticide composition of claim 1, wherein the amount of the alkylpolysaccharide is between 3.6 and 7.6 weight percent of the pesticide composition.

\* \* \* \* \*